(12) United States Patent
Sekizawa et al.

(10) Patent No.: US 7,469,608 B2
(45) Date of Patent: Dec. 30, 2008

(54) DISSOLUTION TESTER

(75) Inventors: Kazutoshi Sekizawa, Hachioji (JP); Masao Yamazaki, Hachioji (JP)

(73) Assignee: JASCO Corporation, Hachioji-shi, Tokyo (JP)

( * ) Notice: Subject to any disclaimer, the term of this patent is extended or adjusted under 35 U.S.C. 154(b) by 179 days.

(21) Appl. No.: 11/383,575

(22) Filed: May 16, 2006

(65) Prior Publication Data

US 2006/0260422 A1 Nov. 23, 2006

(30) Foreign Application Priority Data

May 17, 2005 (JP) .............................. 2005-144170

(51) Int. Cl.
*G01N 33/00* (2006.01)
(52) U.S. Cl. ........................................ 73/866; 366/286
(58) Field of Classification Search .................. 73/866; 422/68.1; 366/286
See application file for complete search history.

(56) References Cited

U.S. PATENT DOCUMENTS

| 4,227,615 | A | * | 10/1980 | Flick | ........................... 215/222 |
| 5,682,001 | A | * | 10/1997 | Hanson et al. | ................. 73/866 |
| 6,817,750 | B1 | * | 11/2004 | Sands | ........................... 366/205 |
| 6,962,674 | B2 | * | 11/2005 | Dean et al. | ................. 422/68.1 |

FOREIGN PATENT DOCUMENTS

JP 2000-283977 10/2000

* cited by examiner

*Primary Examiner*—Hezron Williams
*Assistant Examiner*—Mark Shabman
(74) *Attorney, Agent, or Firm*—Rankin, Hill & Clark LLP

(57) ABSTRACT

A dissolution tester comprising: a circular water tank having a circular cross section the tank being disposed on a base and containing constant-temperature water; a head disposed above the circular water tank, which moves up and down relative to the base; a cantilever arm for supporting the head in a cantilevered fashion and for moving the head up and down relative to the base; a vessel in which a sample and a test liquid are placed, a desired portion of the vessel being immersed into the constant-temperature water in the circular water tank; and a test-liquid agitator suspended from the head, for agitating the sample and the test liquid inside the vessel.

11 Claims, 7 Drawing Sheets

DISSOLUTION TESTER

RELATED APPLICATIONS

This application claims priority to the Japanese Patent Application 2005-144170 dated on May 17, 2005 and is hereby incorporated with reference for all purposes.

BACKGROUND OF THE INVENTION

1. Field of the Invention

The present invention relates to dissolution testers, and more particularly, to an improved stabilizing mechanism therefor.

2. Prior Art

Conventionally, in order to ensure consistent quality of drug samples, dissolution tests are conducted to test the dissolution of compounds of interest from those samples.

Various different kinds of dissolution testers have been developed for conducting such tests. For example, one such dissolution tester in the related art is the device described in Japanese Unexamined Patent Application Publication No. 2000-283977.

Dissolution testers generally include a vessel, a paddle (or a rotating basket), a rotary shaft, an electric motor, and a constant-temperature-water tank.

In a dissolution test, a typical sequence of operations carried out with the dissolution tester is as follows. A fixed amount of test liquid is placed in the vessel and the temperature of the test liquid in the vessel is maintained at 37±5° C. Then, after immersing a sample to the center at the bottom of the vessel, the paddle is rotated at a specified position The test liquid is then collected from the vessel after a specified period of time; this is known as the sample solution. The compounds of interest in the sample solution are then measured using a specified method, and a dissolution rate corresponding to the indicated amount is obtained.

It is essential to ensure stability of the dissolution test.

However, in dissolution testers using conventional techniques, it is difficult to further stabilize the dissolution test. In addition, the factors preventing further stabilization of the dissolution test with the conventional techniques are not well known.

SUMMARY OF THE INVENTION

The present invention has been conceived in light of the above-described problems in the related art. An object thereof is to provide a dissolution tester that can conduct a dissolution test more stably.

The present invention has been conceived in consideration of the points described below.

<Investigation of Factors Involved>

As a result of extensive investigation into the factors involved in conducting a stable dissolution test, the inventors of the present invention discovered the following problems preventing further stabilization of the dissolution test.

Namely, in order to further stabilize the dissolution test, the inventors found that it is extremely important to control the temperature of the test liquid in the vessel during the dissolution test.

In practice, however, the test liquid is easily affected by the temperature of the surroundings, and the phenomenon described below was observed.

The dissolution test is normally conducted using a plurality of vessels simultaneously, rather than a single vessel. In this case, however, it was found that it is sometimes not possible to conduct the dissolution test stably due to temperature differences between the test liquids in the vessels.

Conventionally, in order to eliminate temperature variations among the vessels, an additional temperature control system has been considered. However, providing a new temperature control system complicates the configuration and may cause additional sources of instability.

Therefore, in the present invention, in order to conduct a stable dissolution test, the most important issue is to make the temperatures of the test liquids in the vessels uniform, using a simple configuration.

The inventors therefore investigated a suitable way of solving this problem and found that the reason for the temperature variations among the vessels was nonuniformity of the temperature of the constant-temperature water, which varied depending on the location inside the constant-temperature-water tank.

In other words, because a rectangular constant-temperature-water tank is generally used in dissolution testers, the water is easily affected by the outside air temperature, especially at the corners of the constant-temperature-water tank, where the effect is extremely strong.

In addition, because the magnitude and direction of convection due to agitation of the constant-temperature water and heat also vary from place to place inside the tank, it is difficult to make the water temperature in the tank uniform.

In order to improve the uniformity of the constant-temperature water using a simple configuration, based on their observation of these phenomena, the inventors of the present invention found that it is extremely important to use a circular water tank as the constant-temperature-water tank, instead of the conventional rectangular water tank. The present invention was thus realized using a circular water tank.

Solving Means

In order to achieve the object described above, a dissolution tester according to the present invention includes a circular water tank whose cross section is circular, a head, a cantilever arm, a vessel, and an agitator.

The circular water tank is provided on a base, and constant-temperature water with a temperature suitable for the dissolution test is held inside.

The head is disposed above the circular water tank and moves up and down relative to the base.

The cantilever arm supports the head in a cantilevered fashion so that it can move up and down relative to the base.

The vessel holds a sample and test liquid, and a desired portion thereof is immersed into the constant-temperature water in the circular water tank.

The agitator is suspended from the head and agitates the sample and the test liquid inside the vessel.

As one example, the test-liquid agitator in the present invention includes a paddle or rotating basket, and a rotary shaft for rotating the paddle or rotating basket.

<Circular Heater>

In the present invention, the circular water tank preferably includes a water-tank main body whose cross section is circular and a circular heater.

The circular heater is disposed concentrically at the inner base of the water-tank main body and adjusts the temperature of the constant-temperature water inside the water-tank main body.

<Constant-Temperature-Water Agitator>

In the present invention, the circular water tank preferably also includes a constant-temperature-water agitator.

The constant-temperature-water agitator is disposed at the bottom center inside the water-tank main body and agitates the constant-temperature water inside the water-tank main body.

<Rotary Attaching and Detaching Mechanism>

It is preferable in the present invention that the water-tank main body is rotatable relative to the base. It is preferable in the present invention that the water-tank main body is attached to and detached from the base by rotating the water-tank main body relative to the base after the test-liquid agitator is moved upwards together with the head to be separated from the vessel.

<Positioning Mechanism>

It is preferable in the present invention that a positioning mechanism may be provided. The positioning mechanism preferably includes a rotating stopper and a stationary stopper.

The positioning mechanism regulates the rotation angle of the water-tank main body relative to the base such that the rotation angle of the water-tank main body relative to the base is a specified angle.

The rotating stopper is provided at a position other than the center at the bottom outside the water-tank main body or on the outer circumferential wall of the water-tank main body, rotates together with the water-tank main body The stationary stopper is provided at a position other than the center of the base, which makes contact with the rotating stopper when the rotation angle of the water-tank main body relative to the base is the specified angle.

<Position Sensor>

It is preferable in the present invention that a position sensor and a permitting device are provided.

The position sensor detects whether or not the stationary stopper and the rotating stopper are making contact The permitting device permits operation of the dissolution tester and peripheral equipment thereof when it is determined that the stationary stopper and the rotating stopper are not in contact, based on detection information from the position sensor.

<Light Shielding>

In the present invention, the vessel preferably comprises a vessel main body into which the sample and the test liquid are placed, and an opening being provided at the top of the vessel main body. In the present invention, a vessel lid is provided and closes the opening at the top of the vessel main body. It is preferable in the present invention that at least the circumferential wall of the circular water tank is brown, red, or orange having high light-shielding characteristics. It is also preferable in the present invention that at least the circumferential wall of the circular water tank is brown, red, or orange absorbing ultraviolet light and short-wavelength visible light. It is also preferable in the present invention that the vessel lid is brown, red, or orange having high light-shielding characteristics. It is also preferable in the present invention that the vessel lid is brown, red, or orange absorbing ultraviolet light and short-wavelength visible light.

Effect

<Circular Water Tank>

Because the dissolution tester according to the present invention includes the head cantilever arm and the circular water tank, it is possible to conduct a dissolution test more stably with a simple configuration.

Disposing the circular heater concentrically at the inner base of the circular water tank in the present invention allows the dissolution test to be conducted more stably.

Providing the constant-temperature-water agitator at the bottom center of the circular water tank allows the dissolution test to be conducted more stably.

<Rotary Attaching and Detaching Mechanism>

In the present invention, attaching and detaching the water-tank main body by rotating it relative to the base allows the dissolution test to be conducted more stably.

Providing the positioning mechanism for positioning the water-tank main body relative to the base in the present invention allows the dissolution test to be conducted more stably.

Providing the position sensor for detecting whether or not the water-tank main body is surely positioned relative to the base in the present invention allows the dissolution test to be conducted more stably.

<Light Shielding>

In the present invention, by making the circular water tank brown, red, or orange, or by making the vessel lid brown, red, or orange, it is possible to conduct the dissolution test more stably.

DESCRIPTION OF THE PREFERRED EMBODIMENT

A preferred embodiment of the present invention will be described below based on the drawings.

Figure 1:
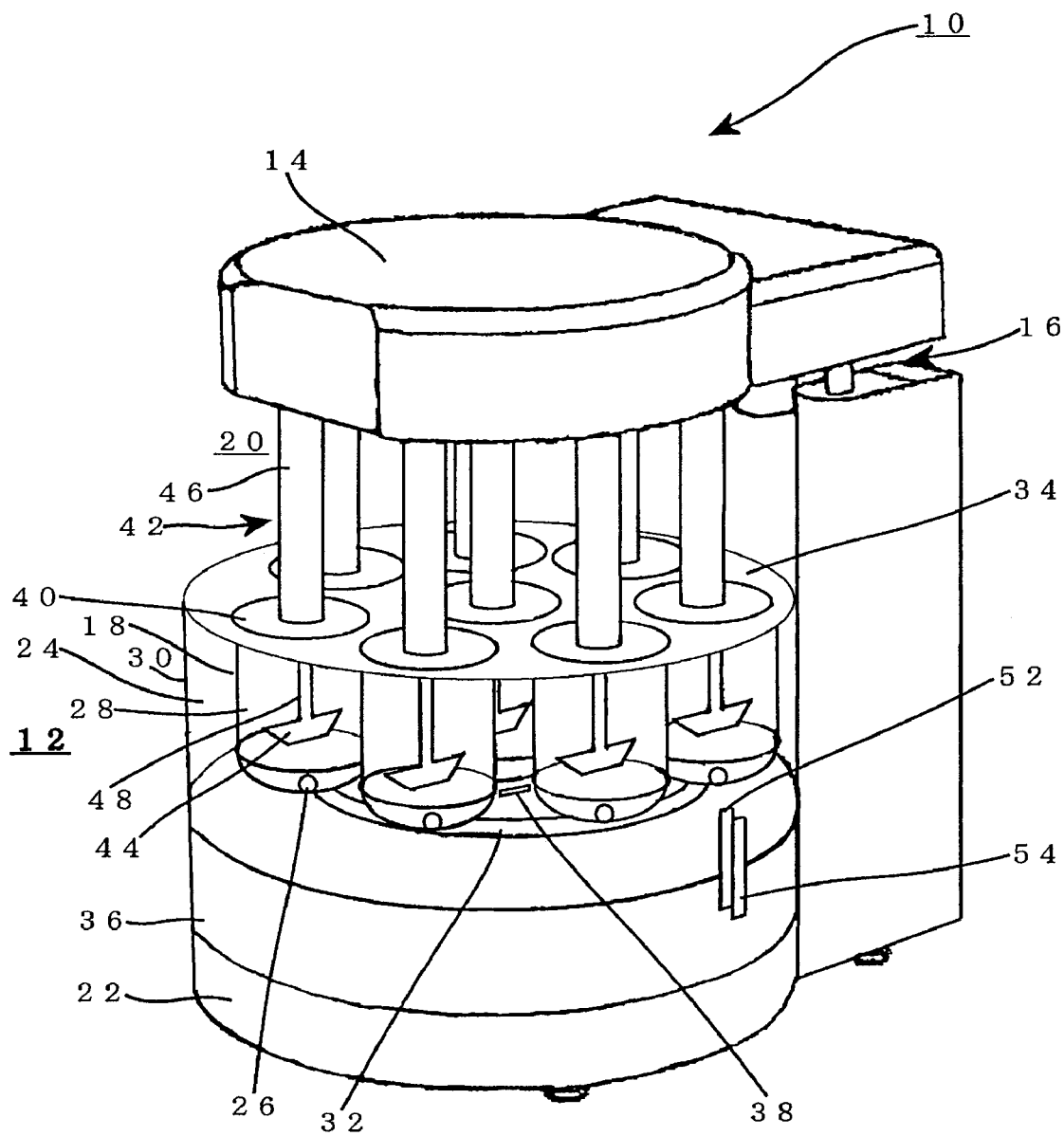
FIG. 1 is a diagram showing an outline configuration of a dissolution tester according to an embodiment of the present invention, during a dissolution test.

FIG. 1 shows, in outline, the configuration of a dissolution tester according to an embodiment of the present invention.

A dissolution tester 10 shown in FIG. 1 includes a circular water tank 12 whose cross section is circular, a head 14, a cantilever arm 16, vessels 18, and test-liquid agitators 20.

The circular water tank 12 is disposed on a base 22 and is filled with constant-temperature water 24.

The head 14 is disposed above the circular water tank 12 and moves up and down relative to the base 22.

The cantilever arm 16 supports the head 14 in a cantilevered fashion in such a manner that it can freely move up and down relative to the base 22.

Desired portions of the vessels 18 can be immersed into the constant-temperature water 24 in the circular water tank 12. The vessels 18 contain samples 26 and test liquids 28 for the dissolution test.

The test-liquid agitator 28 is suspended from the lower end of the head 14 and agitates the samples 26 and the test liquids 28 in the vessels 18.

<Circular Water Tank>

In this embodiment, the circular water tank 12 preferably includes a water-tank main body 30 whose cross section is circular, a circular heater 32, and a water-tank lid 34.

The water-tank main body 30 is made of plastic, for example. The water-tank main body 30 is mounted on the base 22, with a circular skirt 36 provided therebetween.

The circular heater 32 is a ring-shaped device provided concentrically on the inner base of the water-tank main body 30. The circular heater 32 regulates the temperature of the constant-temperature water 24 inside the water-tank main body 30 to a temperature of about 37 degrees Celsius, for example.

The water-tank lid 34 has a circular cross section and is made of stainless steel, for example. The water-tank lid 34 holds the vessels 18 in the water-tank main body 30 so that the desired portions of the vessels 18 are immersed in the constant-temperature water 24 in the water-tank main body 30.

The vessels 18 are separated from the wall of the circular water tank 12. Each vessel 18 is disposed as described below, for instance.

In this embodiment, the vessels 18 are disposed so that one of the vessels 18 is located at the center of the circular water tank 12 and the seven other vessels 18 are disposed at equally spaced intervals around a concentric circle.

In this embodiment, the circular heater 32 is used as a heater. The circular heater 32 forms a circle (ring shape) disposed at a position below the seven outer vessels 18. The diameter of the circular heater 32 is slightly smaller than the diameter of a circle drawn through the centers of the seven outer vessels 18.

The circular water tank 12 preferably also includes a constant-temperature-water agitator 38.

The constant-temperature-water agitator 38 is disposed at the center of the base inside the water-tank main body 30 and agitates the constant-temperature water 24 inside the water-tank main body 30.

<Vessels>

In the present embodiment, the vessels 18 are provided with vessel lids 40.

The vessel lids 40 are disc-shaped objects that can be freely attached to and removed from the openings at the top of the vessels 18. The vessel lids 40 prevent evaporation of the test liquids 28.

<Test-Liquid Agitators>

In this embodiment, the test-liquid agitators 20 each include a lid-moving shaft 42 and a paddle 44.

The lid-moving shafts 42 are suspended from the lower end of the head 14, hold the centers of the vessel lids 40, and move up and down together with the head 14.

The lid-moving shafts 42 each include a tube 46 and a rotating shaft 48.

The tubes 46 are secured to the head 14, and the outer walls thereof are secured to the centers of the vessel lids 40.

The rotating shafts 48 are disposed inside the tubes 46 so that they can rotate, and the paddles 44 are provided at the lower portions thereof.

The paddles 44 rotate together with the rotating shafts 48 to agitate the samples 26 and the test liquids 28 inside the vessels 18.

By structuring the dissolution tester 10 in this way, it is possible to conduct a dissolution test.

In order to stably conduct a dissolution test using the dissolution tester 10, it is extremely important to stabilize the temperature inside the vessels 18. Although heaters or similar devices are conventionally used, it is difficult to expect further temperature stabilization.

In contrast, by investigating the origin of the temperature variations in the vessels 18, as described above, this embodiment solves the problem by means of the circular water tank 12.

Figure 2A:
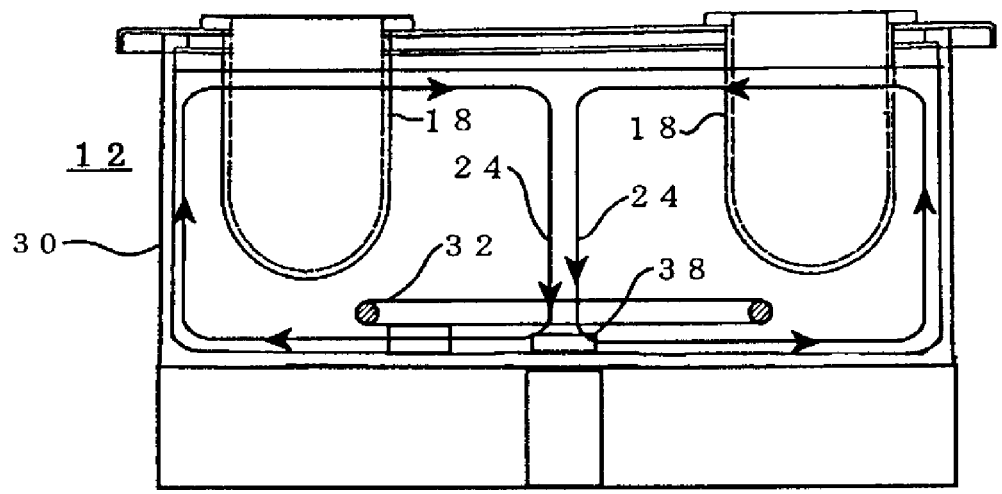
FIGS. 2A and 2B are diagrams of an outline configuration and an operation of a circular water tank, which is a characterizing feature of this embodiment.
Figure 2B:
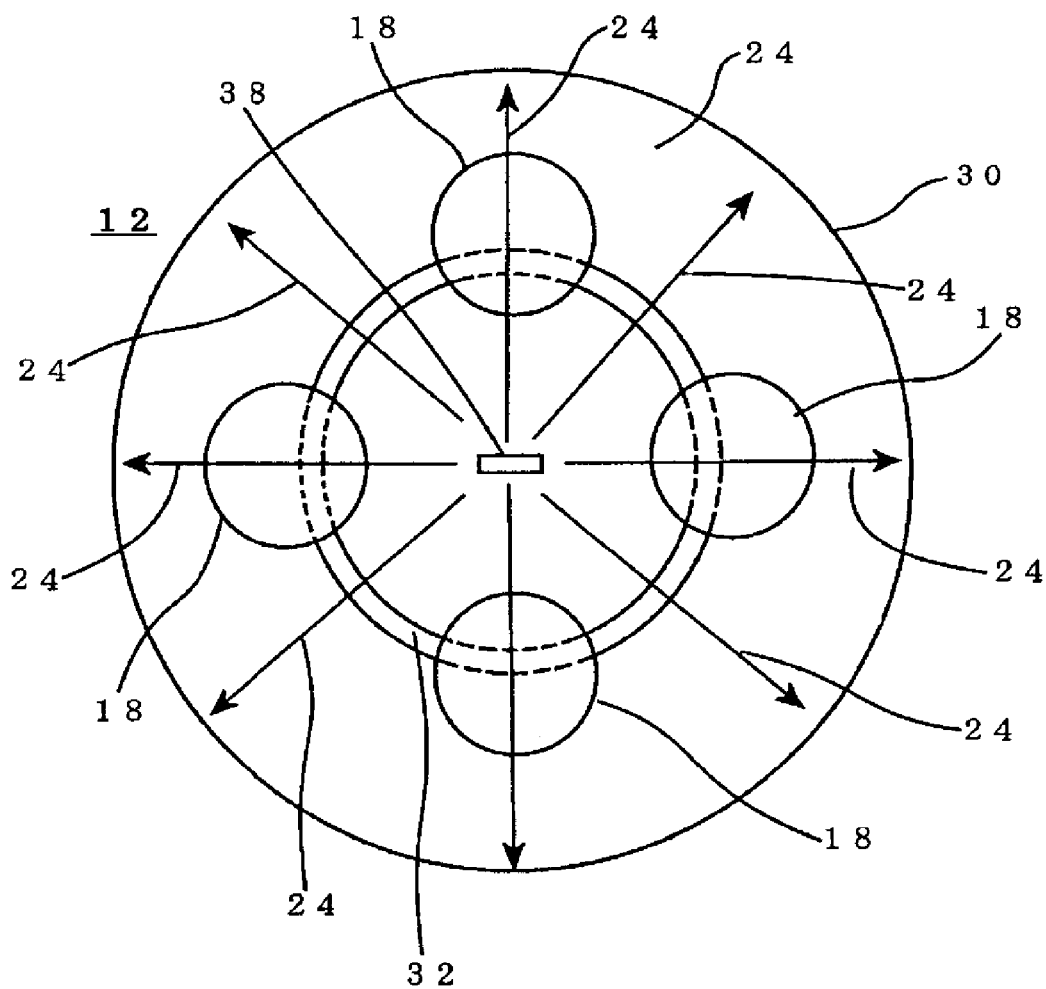

A simplified model of the circular water tank 12 is shown in FIGS. 2A and 2B. FIG. 2A is a side view of the circular water tank 12, and FIG. 2B is a top view of the circular water tank 12.

The circular water tank 12 shown in FIGS. 2A and 2B serves as a constant-temperature-water tank in this embodiment. Vessels 18 are placed inside the circular water tank 12 so as to be separated from the wall thereof. In this embodiment, the plurality of vessels 18 are located at regular intervals around a concentric circle.

The heater in this embodiment is a circular heater 32. In this embodiment, the circular heater 32 forms a circle (ring shape) disposed at a position below the vessels 18. The diameter of the circular heater 32 is slightly smaller than that of a circle drawn through the centers of the plurality of vessels 18.

A constant-temperature-water agitator 38 is disposed at the center of the bottom of the circular water tank 12.

As a result, providing the circular water tank 12 and the circular heater 32 in this embodiment gives rise to convection of the constant-temperature water 24, which is heated by the circular heater 32, with axial symmetry about the center of the circular water tank 12.

More specifically, the constant-temperature water 24 at the center at the bottom of the circular water tank 12 is made to flow from the center at the bottom of the circular water tank 12 towards the wall by the constant-temperature-water agitator 38. Upon reaching the wall, the constant-temperature water 24 rises upwards along the wall and eventually reaches the top surface. Once it has reached the top surface, the constant-temperature water 24 then falls substantially at the center until it again reaches a vicinity of the constant-temperature-water agitator 38. In this embodiment, the constant-temperature water 24 circulates in this way inside the circular water tank 12.

Because of the circular water tank 12 in this embodiment, it is difficult for the outside air temperature to have any effect.

Therefore, any temperature nonuniformities from location to location inside the circular water tank 12 are eliminated in this embodiment, and the temperature of the constant-temperature water 24 inside the circular water tank 12 can thus be kept uniform. Because temperature nonuniformities inside the vessels 18 can be eliminated in this embodiment, it is possible to conduct the dissolution test stably.

Rotary Attaching and Detaching Mechanism>

Ease of use and positional reproducibility during maintenance of the dissolution tester are also important.

Figure 3:
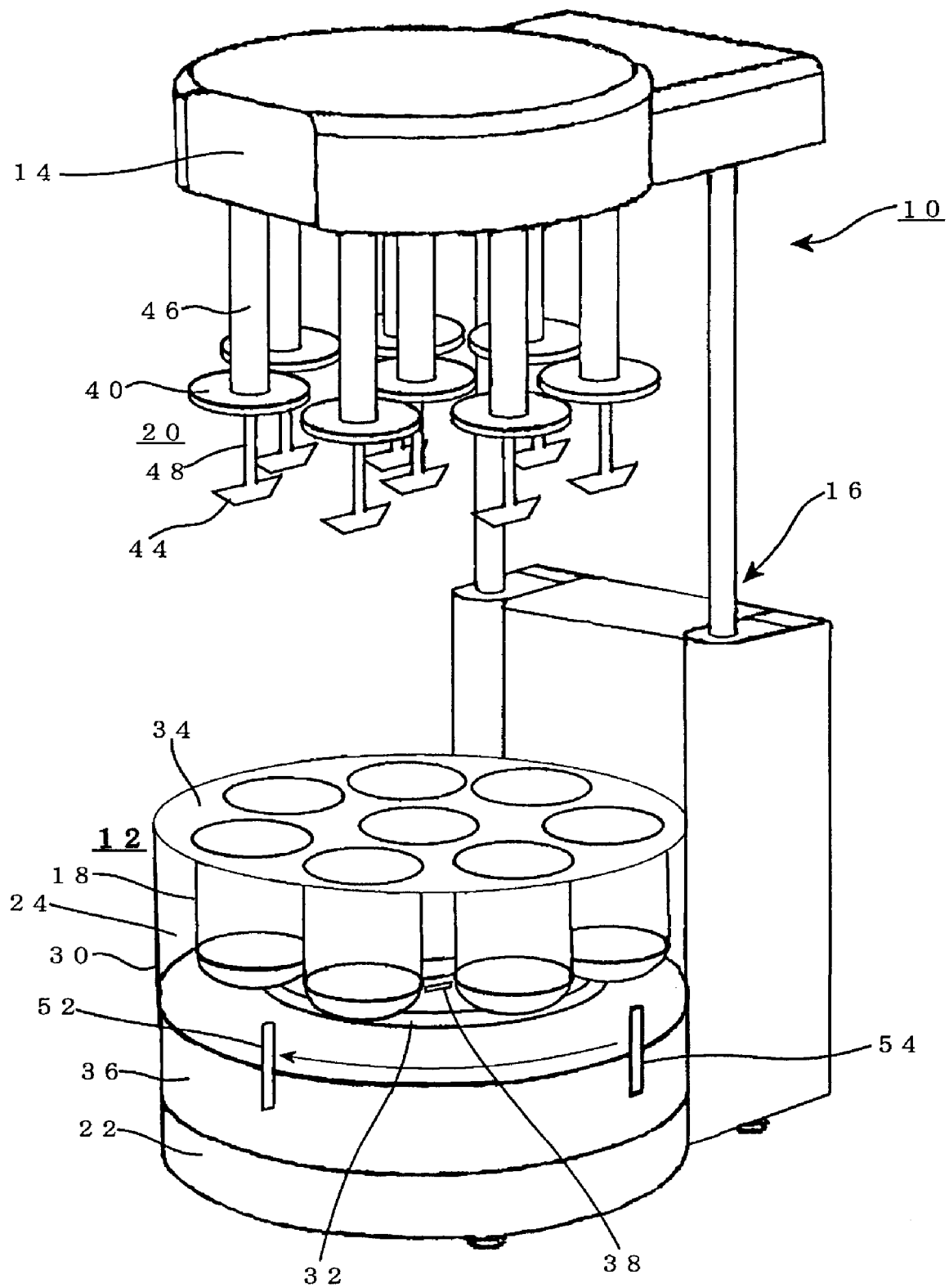
FIG. 3 is a diagram showing an outline configuration of the dissolution tester according to the embodiment of the present invention, during maintenance.

Accordingly, as shown in FIG. 3, the water-tank main body 30 in this embodiment is provided in such a manner that it can be freely rotated relative to the base 22.

During maintenance, the test-liquid agitators 20 are moved upwards, together with the head 14, to separate them from the vessels 18, as shown in FIG. 3.

In this embodiment, it is preferable that the water-tank main body 30 be freely attachable to and detachable from the base 22 by rotating the water-tank main body 30 relative to the base 22.

<Stoppers>

In this embodiment, the water-tank main body 30 of the circular water tank 12 must be reset into position after removing it. It is important to ensure good positioning reproducibility and ease of use when doing so.

Figure 4A:
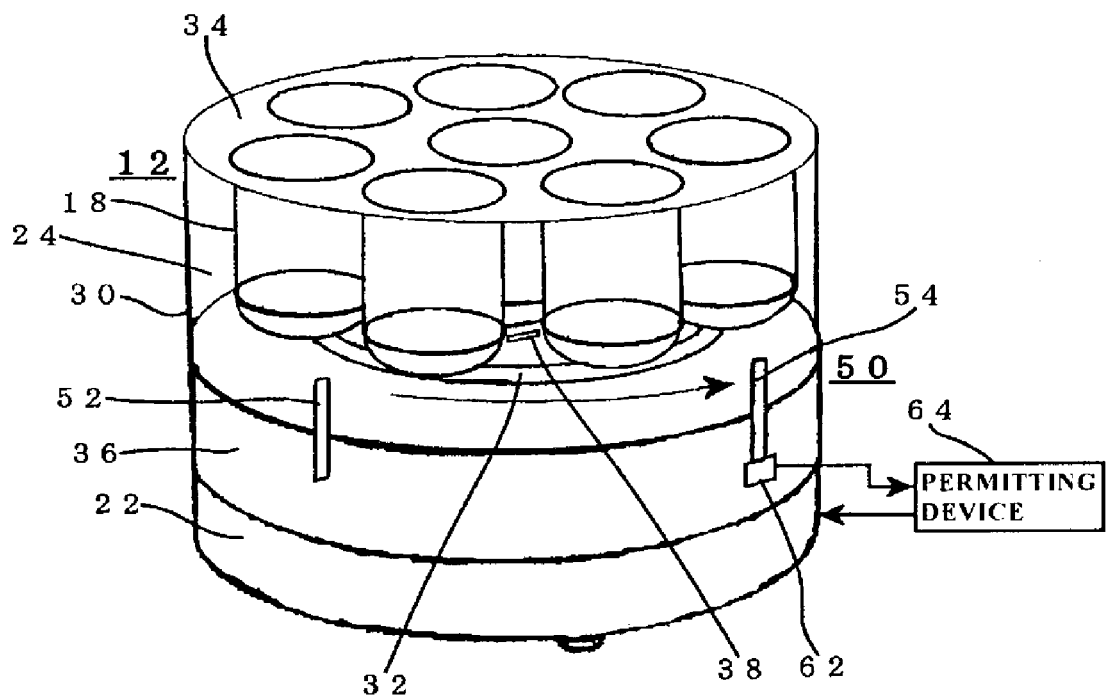
FIGS. 4A and 4B are diagrams of a rotary attaching and detaching mechanism for the circular water tank, which is the characterizing feature of this embodiment.

In order to accomplish this, as shown in FIG. 4A, a positioning mechanism 50 is provided in this embodiment.

The positioning mechanism 50 preferably includes a rotating stopper 52 and a stationary stopper 54.

The positioning mechanism 50 regulates the rotation angle of the water-tank main body 30 relative to the base 22 so that the rotation angle of the water-tank main body 30 relative to the base 22 is a specific angle.

The rotating stopper 52 is provided at a location other than the center of the outer base of the water-tank main body 30 or on the outer circumferential wall of the water-tank main body 30, and is rotated together with the water-tank main body 30.

The stationary stopper 54 is provided at a location other than the center of the base 22. The stationary stopper 54 makes contact with the rotating stopper 52 when the rotation angle of the water-tank main body 30 relative to the base 22 reaches the specific angle.

Figure 4B:
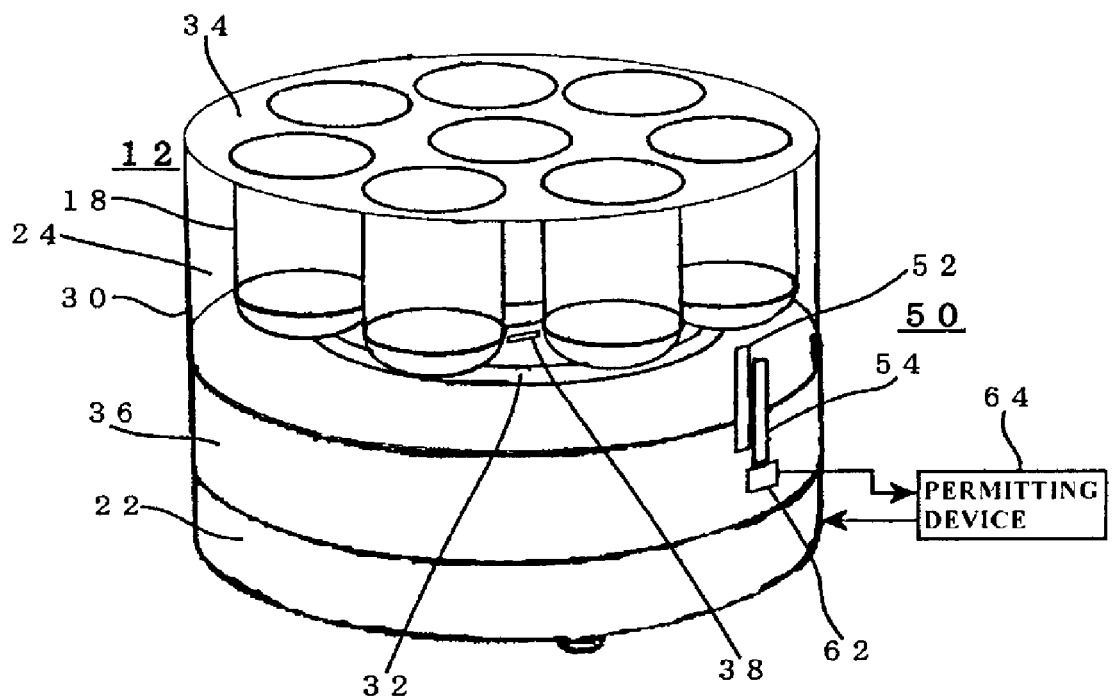

In this embodiment, when the water-tank main body 30 is rotated as shown in FIG. 4A, and when the water-tank main body 30 is set at a desired angle relative to the base 22, as shown in FIG. 4B, the stationary stopper 54 and the rotating stopper 52 make contact, which stops the rotation of the water-tank main body 30.

In this way, when setting the water-tank main body 30 at the desired angle, predetermined positioning is accomplished simply by rotating the water-tank main body 30 until the stationary stopper 54 and the rotating stopper 52 make contact. Therefore, the ease of use and reproducibility during this positioning operation can be improved.

As shown in FIGS. 4A and 4B, the circular water tank 12 in this embodiment is provided on the base 22, with the circular skirt 36 disposed therebetween. Accordingly, the stationary stopper 54 is provided on the circular skirt 36.

<Restricting Mechanism>

In order to more stably conduct the dissolution test, it is also important to start the dissolution test once the water-tank main body 30 has been properly positioned relative to the base 22.

Therefore, in this embodiment, it is preferable to provide a position sensor 62 and a permitting device 64.

The position sensor 62 detects whether or not the stationary stopper 54 and the rotating stopper 52 are making contact.

If it is determined that the stationary stopper 54 and the rotating stopper 52 have not made contact based on detection information from the position sensor 62, the permitting device 64 stops the operation of the dissolution tester 10 and its peripheral equipment. Conversely, if it is determined that the stationary stopper 54 and the rotating stopper 52 are making contact based on the detection information from the position sensor 62, the permitting device 64 permits operation of the dissolution tester 10 and its peripheral equipment.

<Electrical Connection>

It is also important to simplify the electrical connection of the dissolution tester 10 when the water-tank main body 30 is removed.

Figure 5:
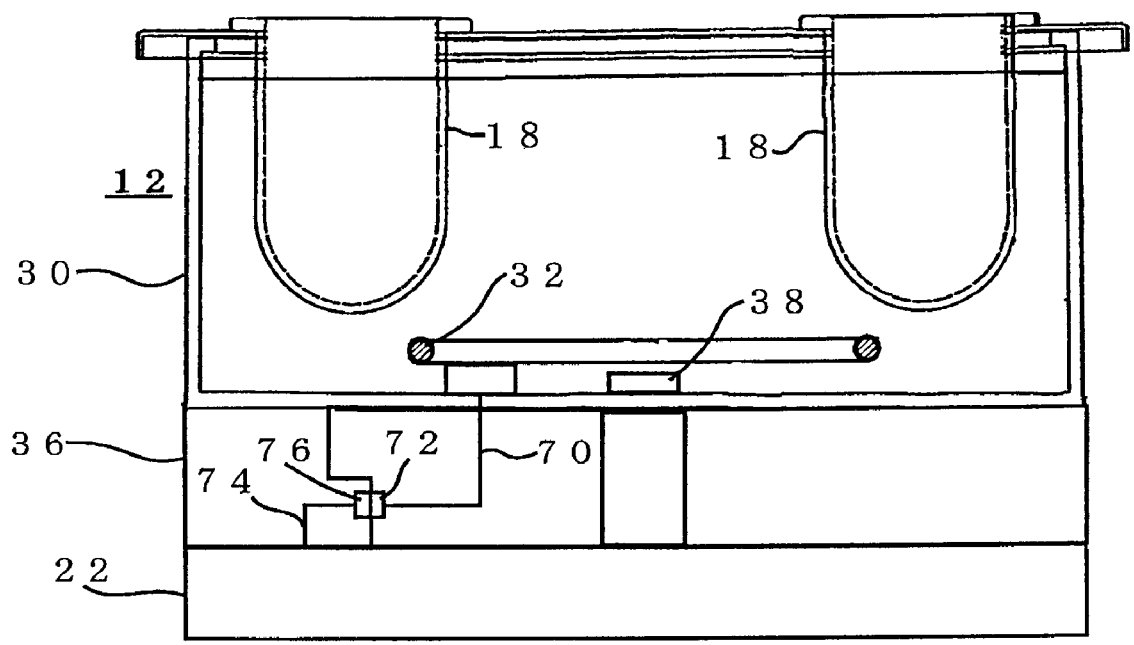
FIG. 5 is a diagram of a connecting mechanism, which is a characterizing feature of the rotary attaching and detaching mechanism shown in FIG. 4.

More specifically, as shown in FIG. 5, electrical wires 70, including heater wires, empty-tank-heating prevention sensor wires, and temperature sensor wires, are led out from the bottom of the water-tank main body 30. The ends of these electrical wires 70 are provided with a connector 72.

In the skirt 36, a connector 76 that can be attached to and detached from the connector 72 is provided on electrical wires 74 for connecting to these electrical wires 70.

In this embodiment, therefore, it is possible to simplify the connection and disconnection when removing the water-tank main body 30 by attaching and detaching the connectors 72 and 76.

Modifications

<Tank Attaching and Detaching Mechanism>

Figure 6:
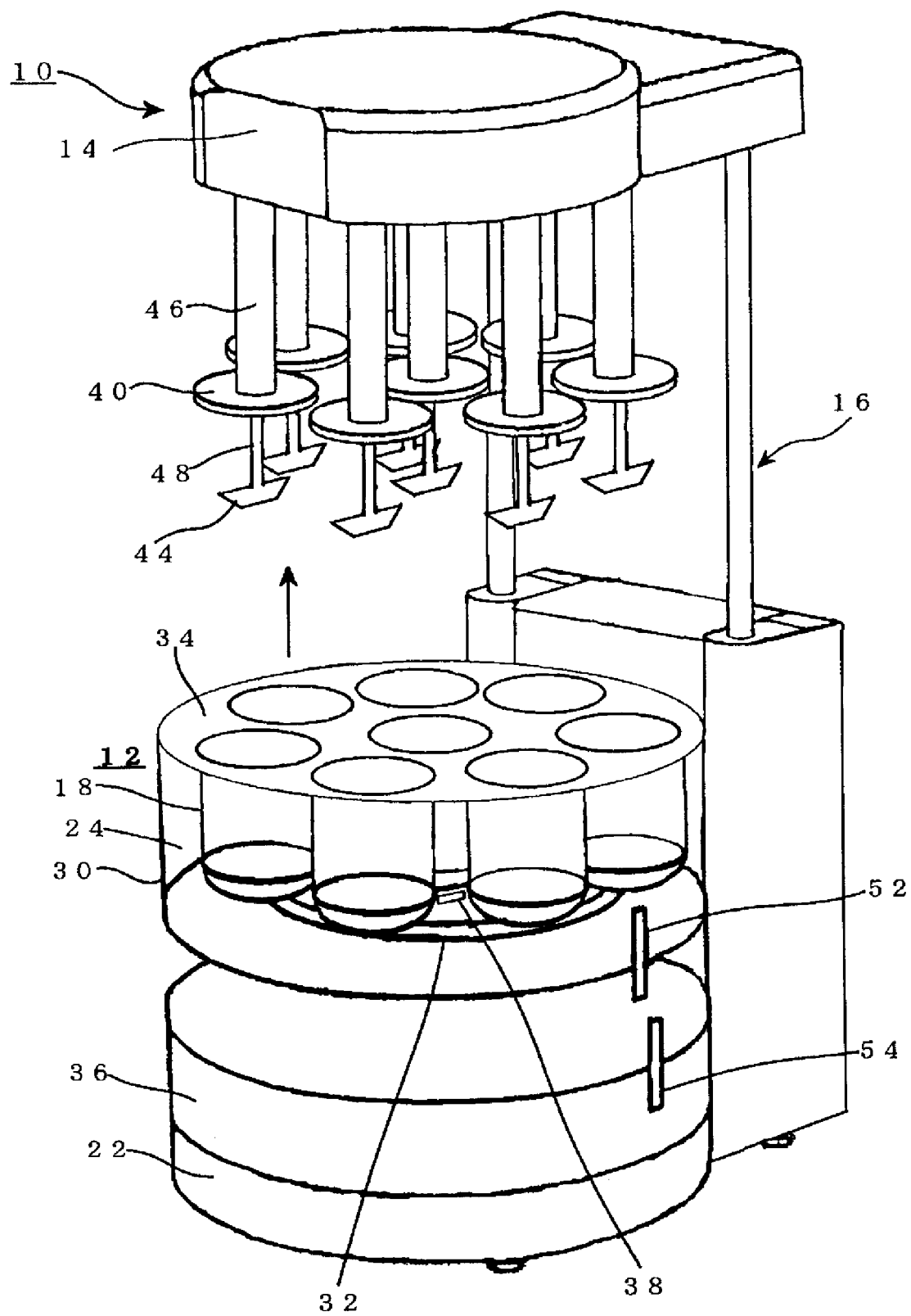
FIG. 6 is a diagram of a modification of the attaching and detaching mechanism shown in FIG. 4.

Although a rotary attaching and detaching mechanism was illustrated in the configuration described above, other types of attaching and detaching mechanisms can also be used. For example, as shown in FIG. 6, a mechanism for raising the water-tank main body 30 relative to the base 22 may be employed in this embodiment.

Figure 7:
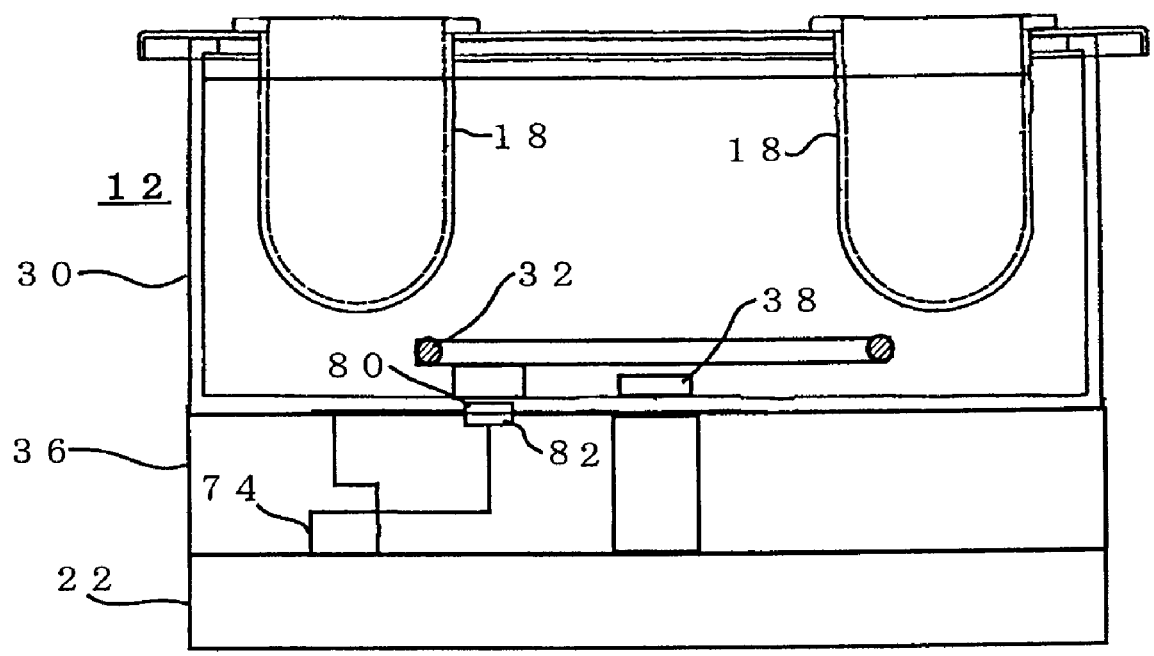
FIG. 7 is a diagram of a connecting mechanism, which is a characterizing feature of the attaching and detaching mechanism shown in FIG. 6.

A connecting mechanism shown in FIG. 7 may also be used in this embodiment. For example, as shown in FIG. 7, a tank-side connector terminal 80 is provided at the bottom of the water-tank main body 30 for heater wires, empty-tank-heating prevention sensor wires, temperature sensor wires, and so on.

A base-side connector terminal 82 for connecting to this tank-side connector terminal 80 is also provided on the skirt 36.

Accordingly, it is possible to automatically connect and disconnect the tank-side connector terminal 80 and the base-side connector terminal 82 simply by attaching and detaching the water-tank main body 30 by moving it downwards and upwards relative to the skirt 36.

It is also possible in this embodiment to employ a mechanism which slides the water-tank main body 30 sideways relative to the base 22.

<Light Shielding>

It is necessary to stabilize the results obtained in the dissolution test.

As a result of extensive investigation into stabilization of the dissolution test results, the present inventors found that the following factors prevent stabilization of the dissolution test.

The constant-temperature-water tank, the vessels, and the vessel lids are usually made of an optically transparent material to allow the inside to be observed. Therefore, if there are substances in the samples whose properties can easily be changed by irradiation with light, their eluted components are sometimes altered in the dissolution test. As a result, conventional methods suffer from the problem that the dissolution test is not stable because the dissolution rate is sometimes observed to change.

Based on the finding that this light sensitivity of the sample is a major factor preventing stabilization of the dissolution test, in the present invention, this problem was solved by providing light shielding on the constant-temperature-water tank and the vessel lids.

A variety of different types of light shielding can be considered. To simplify the configuration, however, it is preferable that at least the outer circumferential wall of the water-tank main body 30 of the circular water tank 12 be made brown, a color which has high light-shielding characteristics. Similarly, it is preferable that the vessel lids 40 also be made brown, a color which has high light-shielding characteristics.

Based on investigation of the factors causing instability in the dissolution test, in this embodiment, a brown-colored tank is used as the water-tank main body 30 of the circular water tank 12. Likewise, brown-colored lids are used as the vessel lids 40 in this embodiment. By doing so, it is possible to stabilize the dissolution test with a simple configuration; this is extremely difficult to achieve with conventional techniques.

In the configuration described above, the water-tank main body 30 of the circular water tank 12 was illustrated using an example in which at least the circumferential wall is brown, a color having high light-shielding characteristics. However, instead of brown, it is also preferable to use red or orange, which also have high light-shielding characteristics.

For the water-tank main body 30 of the circular water tank 12, it is preferable to use a material that absorbs ultraviolet light and short-wavelength visible light. This material is preferably also brown, red, or orange.

The above configuration has been described using an example in which the vessel lids 40 are also brown, a color having high light-shielding characteristics, similarly to the water-tank main body 30 of the circular water tank 12. However, instead of brown, it is also preferable to use red or orange, which also have high light-shielding characteristics.

For the vessel lids 40, it is preferable to use a material that absorbs ultraviolet light and short-wavelength visible light. This material is preferable also brown, red, or orange.

<Measurement Method>

The above configurations have been illustrated by using paddles as the test-liquid agitators; instead of paddles, however, it is also preferable to provide rotating baskets on rotary shafts. With this configuration, it is preferable to place tablets inside the rotating baskets and to agitate the drug by rotating the baskets using the rotary shafts.

<Dosage Form>

The above configurations were illustrated by using tablets as the dosage form of the samples; however, it is also preferable to use other suitable dosage forms, such as capsules, granules, or powder.

What is claimed is:

1. A dissolution tester comprising:
   a circular water tank having a circular cross section, the tank being disposed on a base and containing constant-temperature water the tank comprising:
   a water-tank main body having a circular cross section and
   a circular heater for regulating the temperature of the constant-temperature water inside the water-tank main body, the circular heater being provided concentrically at the bottom inside the water-tank main body;
   a head disposed above the circular water tank, which moves up and down relative to the base;
   a cantilever arm for supporting the head in a cantilevered fashion and for moving the head up and down relative to the base;
   a vessel in which a sample and a test liquid are placed, a desired portion of the vessel being immersed into the constant-temperature water in the circular water tank;
   a test-liquid agitator suspended from the head, for agitating the sample and the test liquid inside the vessel; and
   an agitator for agitating the constant-temperature water inside the water-tank main body, the agitator being provided at a center at the bottom inside the water-tank main body.

2. The dissolution tester of claim 1, wherein the water-tank main body is rotatable relative to the base, and the water-tank main body is attached to and detached from the base by rotating the water-tank main body relative to the base after the test-liquid agitator is moved upwards together with the head to be separated from the vessel.

3. The dissolution tester of claim 1, wherein the water-tank main body is rotatable relative to the base, and the water-tank main body is attached to and detached from the base by rotating the water-tank main body relative to the base after the test-liquid agitator is moved upwards together with the head to be separated from the vessel.

4. The dissolution tester of claim 1, wherein the water-tank main body is rotatable relative to the base, and the water-tank main body is attached to and detached from the base by rotating the water-tank main body relative to the base after the test-liquid agitator is moved upwards together with the head to be separated from the vessel.

5. The dissolution tester of claim 2, further comprising:
   a positioning mechanism for regulating the rotation angle of the water-tank main body relative to the base such that the rotation angle of the water-tank main body relative to the base is a specified angle,
   wherein the positioning mechanism comprises
   a rotating stopper provided at a position other than the center at the bottom outside the water-tank main body or on the outer circumferential wall of the water-tank main body, for rotating together with the water-tank main body; and
   a stationary stopper provided at a position other than the center of the base, which makes contact with the rotating stopper when the rotation angle of the water-tank main body relative to the base is the specified angle.

6. The dissolution tester of claim 3, further comprising:
   a positioning mechanism for regulating the rotation angle of the water-tank main body relative to the base such that the rotation angle of the water-tank main body relative to the base is a specified angle,
   wherein the positioning mechanism comprises
   a rotating stopper provided at a position other than the center at the bottom outside the water-tank main body or on the outer circumferential wall of the water-tank main body, for rotating together with the water-tank main body; and
   a stationary stopper provided at a position other than the center of the base, which makes contact with the rotating stopper when the rotation angle of the water-tank main body relative to the base is the specified angle.

7. The dissolution tester of claim 4, further comprising:
   a positioning mechanism for regulating the rotation angle of the water-tank main body relative to the base such that the rotation angle of the water-tank main body relative to the base is a specified angle,
   wherein the positioning mechanism comprises
   a rotating stopper provided at a position other than the center at the bottom outside the water-tank main body or on the outer circumferential wall of the water-tank main body, for rotating together with the water-tank main body; and
   a stationary stopper provided at a position other than the center of the base, which makes contact with the rotating stopper when the rotation angle of the water-tank main body relative to the base is the specified angle.

8. The dissolution tester of claim 5, further comprising:
   a position sensor for detecting whether or not the stationary stopper and the rotating stopper are making contact; and
   a permitting device for permitting operation of the dissolution tester and peripheral equipment thereof when it is determined that the stationary stopper and the rotating stopper are in contact with one another, based on detection information from the position sensor.

9. The dissolution tester of claim 6, further comprising:
   a position sensor for detecting whether or not the stationary stopper and the rotating stopper are making contact; and
   a permitting device for permitting operation of the dissolution tester and peripheral equipment thereof when it is determined that the stationary stopper and the rotating stopper are in contact with one another, based on detection information from the position sensor.

10. The dissolution tester of claim 7, further comprising:
    a position sensor for detecting whether or not the stationary stopper and the rotating stopper are making contact; and
    a permitting device for permitting operation of the dissolution tester and peripheral equipment thereof when it is determined that the stationary stopper and the rotating stopper are in contact with one another, based on detection information from the position sensor.

11. The dissolution tester of claim 1, wherein the vessel comprises:
- a vessel main body into which the sample and the test liquid are placed, an opening being provided at the top of the vessel main body; and
- a vessel lid provided for closing the opening at the top of the vessel main body,
- at least the circumferential wall of the circular water tank is brown, red, or orange having high light-shielding characteristics, or brown, red, or orange absorbing ultraviolet light and short-wavelength visible light; and
- the vessel lid is brown, red, or orange having high light-shielding characteristics, or brown, red, or orange absorbing ultraviolet light and short-wavelength visible light.

* * * * *